(12) United States Patent
You et al.

(10) Patent No.: US 7,943,599 B2
(45) Date of Patent: May 17, 2011

(54) SESAMOL DERIVATIVES OR THEIR SALTS, THE PROCESS FOR PREPARING THE SAME, AND THE SKIN EXTERNAL COMPOSITION CONTAINING THE SAME

(75) Inventors: Jae Won You, Seoul (KR); Ho Sik Rho, Yongin-si (KR); Duck Hee Kim, Seoul (KR); Ih Seop Chang, Yongin-si (KR); Ok Sub Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 729 days.

(21) Appl. No.: 11/921,180

(22) PCT Filed: May 29, 2006

(86) PCT No.: PCT/KR2006/002037
§ 371 (c)(1),
(2), (4) Date: Mar. 18, 2008

(87) PCT Pub. No.: WO2006/132479
PCT Pub. Date: Dec. 14, 2006

(65) Prior Publication Data
US 2009/0131686 A1    May 21, 2009

(30) Foreign Application Priority Data
Jun. 8, 2005  (KR) ........................ 10-2005-0048717

(51) Int. Cl.
*A61K 31/66*   (2006.01)
*C07F 9/12*    (2006.01)

(52) U.S. Cl. ........................................ 514/100; 549/220
(58) Field of Classification Search .................. 549/220; 514/100
See application file for complete search history.

(56) References Cited

U.S. PATENT DOCUMENTS
4,499,115 A * 2/1985 Minh et al. .................... 426/546

OTHER PUBLICATIONS
International Search Report for PCT/KR2006/002037 mailed Sep. 28, 2006.

* cited by examiner

*Primary Examiner* — Bernard Dentz
(74) *Attorney, Agent, or Firm* — Nixon & Vanderhye P.C.

(57) ABSTRACT

The present invention relates to a sesamol derivative or its salt, and a skin external composition containing the same. More particularly, the invention relates to a sesamol derivative or its salt, which consists of sesamol and 3-aminopropane phosphoric acid, linked with each other by a phosphoric acid diester bond, and can be degraded into sesamol and 3-aminopropane phosphoric acid by enzymes present on the skin so as to simultaneously show the physiological activities of sesamol and 3-aminopropane phosphoric acid, as well as a preparation method thereof and a skin external composition containing the same.

6 Claims, 1 Drawing Sheet

FIGURES

SESAMOL DERIVATIVES OR THEIR SALTS, THE PROCESS FOR PREPARING THE SAME, AND THE SKIN EXTERNAL COMPOSITION CONTAINING THE SAME

This application is the U.S. national phase of International Application No. PCT/KR2006/002037 filed May 29, 2006 which designated the U.S. and claims priority to Korean Patent Application No. 10-2005-0048717 filed Jun. 8, 2005, the entire contents of each of which are hereby incorporated by reference.

TECHNICAL FIELD

The present invention relates to a sesamol derivative represented by Formula (I), or its salt, as well as a preparation method thereof and a skin external composition containing the same, and more particularly to a sesamol derivative or its salt, which consists of sesamol and 3-aminopropane phosphoric acid, linked with each other by a phosphoric acid diester bond, and can be degraded into sesamol and 3-aminopropane phosphoric acid by enzymes present on the skin so as to simultaneously show the physiological activities of sesamol and 3-aminopropane phosphoric acid, as well as a preparation method thereof and a skin external composition containing the same.

[Formula I]

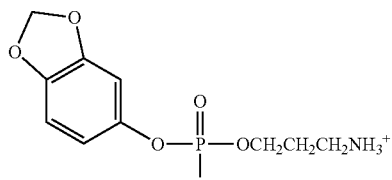

(I)

BACKGROUND ART

The function of cosmetics is to make the skin and hair clean, beautiful and healthy. Particularly, many studies to prevent the formation of wrinkles on the skin through antioxidant activity have been carried out, and many substances for this prevention have been developed and used. These substances include vitamins such as ascorbic acid and tocopherol, and flavonoids extracted from various animals and plants.

Sesamol, a naturally occurring potent antioxidant substance, is the main component of sesame seed oil. It is known that sesame oil is not prone to oxidation compared to other oils due to the antioxidant effects of sesamol. However, despite various antioxidant effects, sesamol has a problem in that it becomes unstable when applied to formulations, as other natural antioxidants do.

Meanwhile, US Patent Publication No. 2004-0121058 discloses a method for extracting an antioxidant from sesamol-containing sesame, and Japanese Patent Publication No. 2001-139944 discloses the synthesis of a sesamol dimer, which has no unpleasant odor or taste and is used as an antioxidant or a whitening agent. However, the introduction of 3-aminopropane phosphoric acid into sesamol has not yet been reported.

DISCLOSURE

Technical Problem

Thus, the present inventors have conducted studies to develop sesamol derivatives, which do not show instability while having antioxidant effects. As a result, the present inventors have synthesized a sesamol derivative, in which 3-aminopropane phosphoric acid and sesamol are linked with each other in the form of phosphoric acid diester, and the inventors have found that these sesamol derivative not only maintains the efficiency of sesamol, but also do not show instability. Also, the present inventors have found that, when the sesamol derivative is administered in vivo, it simultaneously shows the aging prevention effect of 3-aminopropane phosphoric acid and the antioxidant effect of sesamol, thereby completing the present invention.

Technical Solution

In one aspect, the present invention provides a sesamol derivative or its salt, which contains a phosphate group having excellent skin affinity, and thus has an excellent antioxidant effect.

In another aspect, the present invention provides a method for preparing said sesamol derivative or its salt.

In still another aspect, the present invention provides a skin external composition containing a sesamol derivative represented by Formula (I), or its salt:

[Formula I]

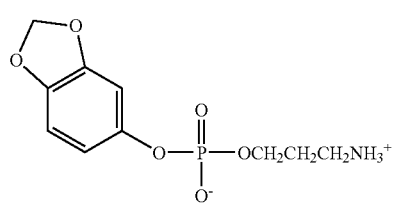

(I)

ADVANTAGEOUS EFFECTS

The inventive sesamol derivative of Formula (I), when applied to the skin, slowly releases sesamol and 3-aminopropane phosphoric acid and do not cause irritation to the skin, and also can be used in cosmetic compositions without limitations. Also, the derivative has potent antioxidant activity in itself, and thus can also be applied in other fields.

Accordingly, the inventive sesamol derivative of Formula (I) can be used in skin external preparations for antioxidant or anti-aging purposes.

BEST MODE

Figure 1:
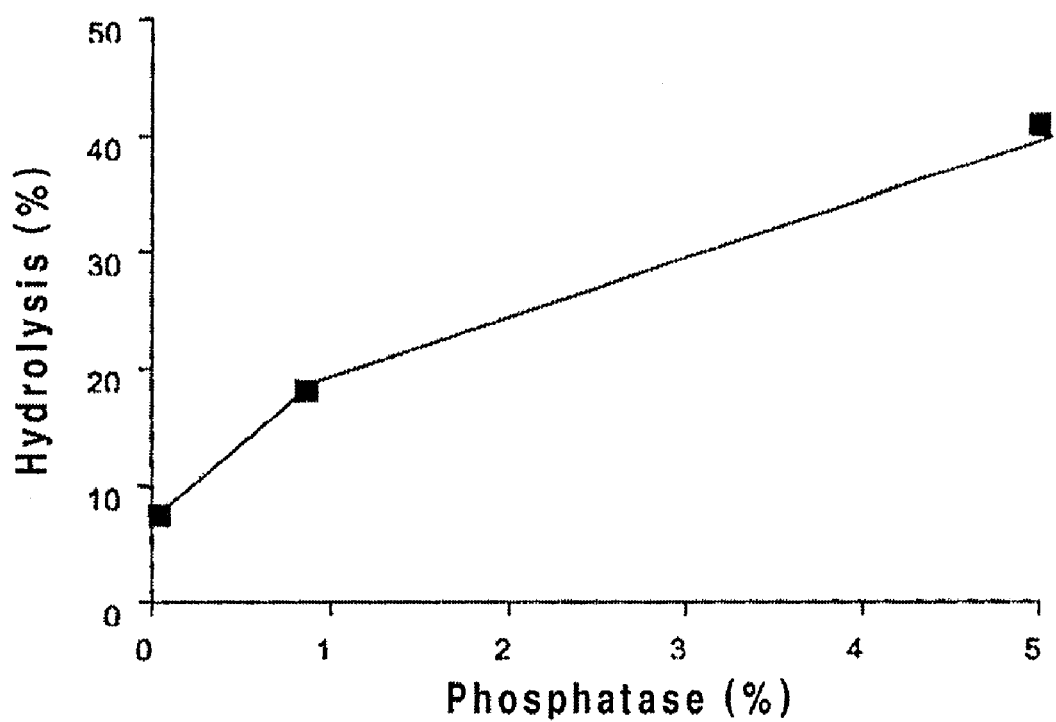
FIG. 1 shows the results of HPLC (high-performance liquid chromatography) analysis for the amount of 3-aminopropane produced by the hydrolysis of sesamol, 3-aminopropane phosphoric acid diester, by phosphatase.

The present invention relates to a sesamol derivative represented by Formula (I), or its salt:

[Formula I]

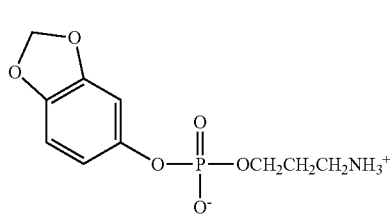

The sesamol derivative shows antioxidant activities similar to those of pure sesamol. Also, said derivative is easily degraded by enzymes in the human body, and thus can simultaneously show the physiological functions of sesamol and 3-aminopropane. Also, the sesamol derivative may also be used in the form of neutralized salts, specific examples of which may include salts of alkali metals such as sodium and potassium, and salts of alkaline earth metals such as calcium.

In another aspect, the present invention relates to a method for preparing a sesamol derivative represented by Formula (I), or its salt, the method comprising: allowing sesamol to react with phosphorus oxychloride in an organic solvent in the presence of an organic base; allowing 3-aminopropanol to react with the reaction product in an organic solvent in the presence of a base; hydrolyzing the reaction product; and then crystallizing the hydrolyzed product with a polar organic solvent.

In still another aspect, the present invention relates to a skin external composition containing the sesamol derivative represented by Formula (I), or a salt thereof.

In said composition, the sesamol derivative or its salt can be contained in an amount of 0.0001-20 wt % based on the total weight of the composition.

The inventive sesamol derivative can be obtained by a preparation method comprising the steps of:

(A) allowing sesamol and phosphorus oxychloride to react with each other at an equivalent ratio of 1:1-1.3 in an organic solvent in the presence of an organic base at a temperature of 12-18° C. for 1-2 hours so as to prepare dichloro[3,4-methylene dioxyphenoxy]-phosphino-1-one;

(B) allowing the dichloro[3,4-methylene dioxyphenoxy]-phosphino-1-one produced in said step (A) to react with 3-aminopropanol in an organic solvent in the presence of a base so as to prepare [3,4-methylene dioxyphenoxy]-1,3,2-oxazaphosphorin P-oxide;

(C) filtering the reaction solution of said step (B), concentrating the filtrate under reduced pressure, allowing the residue to react with an acid solution at a temperature of 5-100° C. for about 8-12 hours to hydrolyze the P—N bond of the residue, thus preparing sesamol, 3-aminopropane phosphoric acid diester (I); and (D) crystallizing the sesamol, 3-aminopropane phosphoric acid diester (I) of said step (C) by slowly adding a polar organic solvent dropwise thereto.

Hereinafter, the present invention will be described in detail.

The method for preparing the sesamol derivative according to the present invention can be schematized by Reaction Scheme I:

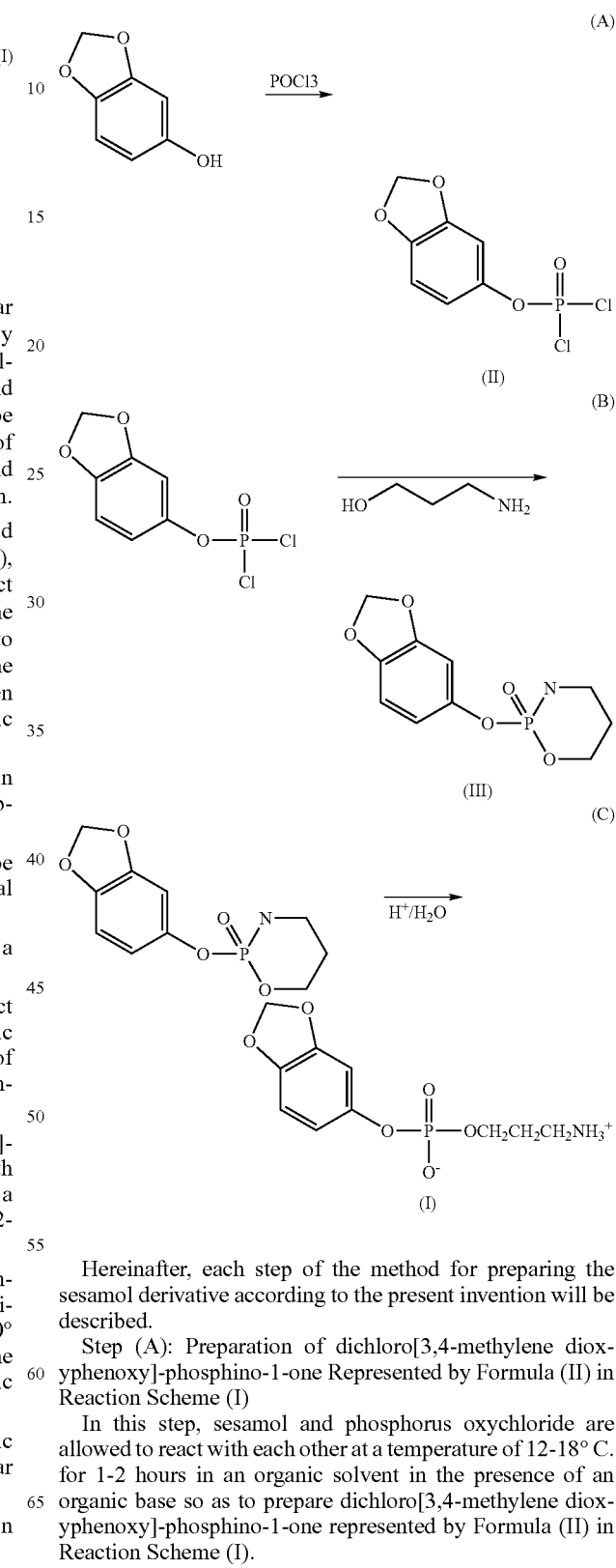

Hereinafter, each step of the method for preparing the sesamol derivative according to the present invention will be described.

Step (A): Preparation of dichloro[3,4-methylene dioxyphenoxy]-phosphino-1-one Represented by Formula (II) in Reaction Scheme (I)

In this step, sesamol and phosphorus oxychloride are allowed to react with each other at a temperature of 12-18° C. for 1-2 hours in an organic solvent in the presence of an organic base so as to prepare dichloro[3,4-methylene dioxyphenoxy]-phosphino-1-one represented by Formula (II) in Reaction Scheme (I).

In this step, sesamol and phosphorus oxychloride are preferably allowed to react at an equivalent ratio of 1:1-1.3. If the equivalent ratio is less than 1:1, the desired product cannot be obtained with good yield, and if it is more than 1:1.3, excess byproducts will be produced in addition to the desired product. When sesamol and phosphorus oxychloride are allowed to react at an equivalent ratio of 1:1-1.3 to prepare dichloro [3,4-methylene dioxyphenoxy]-phosphino-1-one, an intermediate, in which sesamol and phosphorus oxychloride are bound with each other at a ratio of 1:1, is produced in an amount of more than 95%, and a byproduct, in which sesamol and phosphorus oxychloride are bound with each other at a ratio of 2:1, is produced in an amount of less than 1-2%. However, said byproduct can be separated using chromatography or can be easily removed using the difference in solubility in toluene. Also, when sesamol and phosphorus oxychloride are allowed to react at a temperature of 12-18° C. for 1-2 hours, there are advantages in that the production of a byproduct resulting from the reaction of sesamol and phosphorus oxychloride at a ratio of more than 2:1 can be prevented, and particularly the number of reaction steps can be reduced, because a step of introducing an ester group or amide group to protect one chloride atom of phosphorus chloride is not required.

Examples of organic bases, which can be used in said step (A), include pyridine, triethylamine and the like. Preferred is triethylamine.

Also, examples of organic solvents, which can be used in said step (A), include dichloromethane, tetrahydrofuran, ethyl acetate, acetonitrile, chloroform, ethyl ether, trichloroethylene, benzene, toluene and the like, toluene being preferred.

Meanwhile, the reaction temperature in said step (A) is preferably in the range of 12-18° C. This is because, at a temperature above 18° C., more than 2 equivalents of sesamol is substituted into phosphorus oxychloride to increase the production of byproducts, and at a temperature below 12° C., the solubility of the reaction substances is decreased to reduce the reaction rate, making the progression of the reaction difficult, and the content of unreacted substances is increased to reduce the reaction yield.

Step (B): Preparation of [3,4-methylene dioxyphenoxy]-1,3,2-oxazaphosphorin P-oxide Represented by Formula (III) in Reaction Scheme In this step, dichloro[3,4-methylene dioxyphenoxy]-phosphino-1-one produced in said step (A) is allowed to react with 3-aminopropanol in an organic solvent in the presence of a base so as to prepare [3,4-methylene dioxyphenoxy]-1,3,2-oxazaphosphorin P-oxide represented by Formula (III) in Reaction Scheme I.

In this step, dichloro[3,4-methylene dioxyphenoxy]-phosphino-1-one produced in said step (A) is preferably allowed to react with 3-aminopropanol at an equivalent ratio 1:1-1.3. If the equivalent ration is less than 1:1, the desired product cannot be obtained, and if it exceeds 1:1.3, excess byproducts will be produced in addition to the desired product.

Examples of bases, which can be used in said step (B), include organic bases as used in said step (A), such as pyridine or triethylamine, and other bases such as sodium, sodium hydroxide and potassium hydroxide. Preferably, triethylamine is used.

Also, examples of organic solvents, which can be used in said step (B), include nonpolar solvents such as dichloromethane, tetrahydrofuran, ethyl acetate, acetonitrile, chloroform and ethyl ether, and polar solvents such as methanol, ethanol and propanol. Preferably, tetrahydrofuran is used.

Step (C): Preparation of sesamol, 3-aminopropane phosphoric acid diester Represented by Formula (I) in Reaction Scheme I In this step, the reaction solution of said step (B) is filtered and the filtrate is concentrated under reduced pressure. Then, the residue is allowed to react with an acid solution at a temperature of 5-100° C. for about 8-12 hours so as to hydrolyze the P—N bond of the residue, thus preparing sesamol, 3-aminopropane phosphoric acid diester represented by Formula (I) in Reaction Scheme I.

In this step, the reaction solution of said step (B) is filtered and the filtrate is concentrated under reduced pressure. The residue can be hydrolyzed in general conditions using strong cation exchange resin (Amberlyst 15), hydrochloric acid or an acid catalyst such as hydrochloric acid or sulfuric acid. In other words, the P-N bond can be hydrolyzed by adding the acid solution to the compound of said step (B) and then allowing the mixture solution to react at an elevated temperature of 5-100° C. for about 8-12 hours. The reaction temperature in this step is about 5-100° C., and preferably 40-60° C. If the reaction temperature is lower than 5° C., the reaction will not occur, and if it is higher than 100° C., byproducts will be produced to reduce the reaction yield. Also, the pH of the acid solution is 1-5, and preferably 2-4. If the pH is below 1, a P—O bond in addition to the P—N bond will be hydrolyzed to produce byproducts, and if the pH exceeds 5, the reaction will not occur.

Step (D): Crystallization of sesamol, 3-aminopropane phosphoric acid diester (I) Produced in Said Step (C)

In this step, the sesamol, 3-aminopropane phosphoric acid diester (I) produced in said step (C) is crystallized by slowly adding a polar organic solvent dropwise thereto.

Examples of polar organic solvents, which can be used for deposition in said step (D), include methanol, ethanol, isopropanol, acetone, tetrahydrofuran, acetonitrile and dioxane, but are not specifically limited thereto.

The sesamol derivative prepared according to said preparation method can also be used in the form of neutralized salts, specific examples of which may include salts of alkali metals such as sodium and potassium, and salts of alkaline earth metals such as calcium.

MODE FOR INVENTION

Hereinafter, the present invention will be described in further detail with reference to examples. It is to be understood, however, that these examples are not to be construed to limit the scope of the present invention.

PREPRATION EXAMPLE 1

Preparation of dichloro[3,4-methylene dioxyphenoxy]-phosphino-1-One 4.5 g (0.03 mol) of phosphorus oxychloride was dissolved in 10 ml of hexane, to which 3 g (0.03 mol) of triethylamine and 20 ml of toluene were then added. The solution was cooled on an ice-water bath to a temperature of 0-5° C. Meanwhile, in another container, 3.12 g (0.02 mol) of sesamol was dissolved in 80 ml (0.73 mol) of toluene, and the sesamol solution was then added dropwise to the above-prepared phosphorus oxychloride dilution over 2 hours. After completion of the addition, the produced triethylammonium chloride was removed. The remaining material was washed with 100 ml of purified water, dried with anhydrous sodium sulfate, filtered and then concentrated under reduced pressure, yielding 4.3 g of dichloro[3,4-methylene dioxyphenoxy]-phosphino-1-one as yellow oil.

$^1$H-NMR(CDCl$_3$): δ(ppm)=5.72 (s, 2H), 6.23 (dd, 1H), 6.43 (d, 1H), 6.64(d, 1H).

EXAMPLE 1

Preparation of sesamol, 3-aminopropane phosphoric acid diester (I)

1.8 g (1.2 equivalents) of 3-aminopropanol and 4.9 g of triethylamine were added to 30 ml of tetrahydrofuran and then stirred at room temperature for 30 minutes. At the same temperature, 2.39 g of dichloro[3,4-methylene dioxyphenoxy]-phosphino-1-one prepared in Preparation Example 1 was slowly added dropwise thereto. After completion of the dropwise addition, the mixture solution was stirred at room temperature overnight, and then the produced triethylammonium chloride was removed. The remaining material was washed with 15% brine, dried with anhydrous sodium sulfate and then filtered. The filtrate was concentrated under reduced pressure and recrystallized from hexane, yielding 2-[3,4-methylene dioxyphenoxy]-1,3,2-oxazaphosphorin P-oxide as a solid.

The above product was dissolved in 30 ml of an aqueous solution (pH 3) and stirred in an incubator at 40° C. for 8 hours. After completion of the stirring, 150 ml of ethanol, acetone or acetonitrile was added to the stirred solution, and the resulting solution was filtered and dried in a vacuum, yielding 2.2 g of sesamol, 3-aminopropane phosphoric acid diester (I) as a solid.

$^1$H-NMR(D$_{2O}$): δ(ppm)=1.82 (m, 2H), 2.97 (t, 2H), 3.86 (q, 2H), 5.79 (s, 2H), 6.48 (dd, 1H), 6.58 (d, 1H), 6.67 (dd, 1H).

EXAMPLE 2

Preparation of sodium salt of sesamol, 3-aminopropane phosphoric acid diester 1 g of sesamol, 3-aminopropane phosphoric acid diester prepared in Example 1 was dissolved in 30 ml of purified water and then adjusted to pH 7 by adding 5% sodium carbonate aqueous solution thereto. The solution was lypophilized, yielding a sodium salt of sesamol, 3-aminopropane phosphoric acid diester as a light yellow solid.

$^1$H-NMR(D$_{2O}$): δ(ppm)=1.86 (m, 2H), 3.01 (t, 2H), 3.89 (q, 2H), 5.79 (s, 2H), 6.42 (dd, 1H), 6.60 (d, 1H), 6.67 (dd, 1H).

EXAMPLE 3

Preparation of potassium salt of sesamol 3-aminopropane phosphoric acid diester 1 g of sesamol, 3-aminopropane phosphoric acid diester prepared in Example 1 was dissolved in 30 ml of purified water and then adjusted to pH 7 by adding 5% potassium carbonate aqueous solution thereto. The solution was lyophilized, yielding a sodium salt of sesamol, 3-aminopropane phosphoric acid diester as a light yellow solid.

$^1$H-NMR(D$_{2O}$): δ(ppm)=1.85(m, 2H), 2.98(t, 2H), 3.86(q, 2H), 5.78(s, 2H), 6.44(dd, 1H), 6.58(d, 1H), 6.67(dd, 1H).

EXPERIMENTAL EXAMPLE 1

Measurement of Antioxidant Effect

Human keratinocytes (HaCat) were plated at a density of $1.0 \times 10^6$ per 60-mm dish and then cultured in penicillin/streptomycin-containing DMEM (10% FBS) media at conditions of 37° C. and 5% $CO_2$ for 1 week. Then, the culture media were treated with $10^{-4}$ M of each of sesamol, the sesamol derivative of Example 1, and tocopherol as appositive control, for 24 hours. At the next day, the media were treated with 4 mM of t-BHP (t-butyl hydroperoxide) together with each of said compounds and then cultured at conditions of 37° C. and 5% $CO_2$ for 4 hours, after which the cells were collected. The collected cells were dissolved by repeatedly performing freezing/thawing processes, and the following tests were performed in accordance with the method described in an assay kit.

In other words, in the present invention, a lipid peroxide assay kit (Calbiochem) was used as a reagent, and lipid peroxidation was measured using the principle in which long-chain unsaturated fatty acids such as malonaldehyde and 4-hydroxy alkenal form stable compounds at 586 nm by reaction with said reagent. The measurement results are shown in Table 1 below in comparison with an untreated group taken as 100.

TABLE 1

| Compounds | Malonaldehyde and 4-hydroxy alkenal |
|---|---|
| Untreated group | 100 |
| t-BHP | 320 |
| Tocopherol | 270 |
| Sesamol | 250 |
| Sesamol derivative of Example 1 | 260 |

As can be seen in Table 1 above, the sesamol, 3-aminopropane phosphoric acid diester (I) according to the present invention showed an antioxidant effect similar to those of sesamol and the positive control tocopherol.

EXPERIMENTAL EXAMPLE 2

Measurement of Anti-Aging Effect

Fibroblasts were seeded into each well of a 24-well plate at density of $10^6$ cells and cultured to 90% confluence. The cultured cells were cultured in serum-free media for 24 hours and then treated with $10^{-4}$ M of each of tocopherol, sesamol and the sesamol derivative of Example 1, which have been dissolved in serum-free media. Then, the cells were cultured in a $CO_2$ incubator for 24 hours. The supernatants of the cell culture media were collected and observed for an increase or decrease in procollagen using a Procollagen type (A) kit. The test results are shown in Table 2 below, in which the effect of each compound on the procollagen synthesis is compared with that of an untreated group, taken as 100%.

TABLE 2

| Compounds | Procollagen Synthesis (%) |
|---|---|
| Untreated group | 100 |
| Tocopherol | 110 |
| Sesamol | 103 |
| Sesamol derivative of Example 1 | 125 |

As can be seen in Table 2 above, the sesamol, 3-aminopropane phosphoric acid diester (I) of the present invention showed the effect of increasing collagen biosynthesis. In other words, it could be observed that the sesamol derivative of the present invention had not only antioxidant effects, but also the effect on the procollagen synthesis. Thus, the sesamol, 3-aminopropane phosphoric acid diester (I) of the present invention can be used for anti-aging purposes.

EXPERIMENTAL EXAMPLE 3

In order to examine whether the sesamol, 3-aminopropane phosphoric acid diester is hydrolyzed by phosphatase present on the skin into sesamol and 3-aminopropane phosphoric acid, the following test was performed. The sesamol, 3-aminopropane phosphoric acid diester of Example 1 and phsophatase were added in phosphate buffer (pH 7.4), followed by hydrolysis. As the phosphatase, alkaline phosphatase commercially available from Sigma-Aldrich Co. was used. The amount of 3-aminopropane phosphoric acid formed as the hydrolysis progressed was measured by HPLC (high-performance liquid chromatography), and the measurement results are shown in FIG. 1.

As can be seen in FIG. 1, it was found that the sesamol, 3-aminopropane phosphoric acid diester can be hydrolyzed by phosphatase present on the skin into sesamol and 3-aminopropane phosphoric acid, so that it can simultaneously the activities of sesamol and 3-aminopropane phosphoric acid.

The sesamol derivative according to the present invention can be used in skin external compositions, and there is no particular limitation on the formulation thereof. For example, it can be formulated into a cosmetic composition such as skin lotion, astringent lotion, milk lotion, nourishing cream, massage cream, essence, eye cream, eye essence, cleansing cream, cleansing foam, cleansing water, pack, powder, body lotion, body cream, body oil, body essence, make-up base, foundation, hair colorant, shampoo, hair conditioner or body washer, or a medical composition such as ointment, gel, cream, patch or spray. Each of these compositions may contain various substrates and additives, which are required and suitable for the formulation thereof, and the kind and amount of each of these components can be easily selected by those skilled in the art.

FORMULATION EXAMPLE 1

Preparation of Milk Lotion

Milk lotion containing the sesamol derivatives prepared in Examples 1-3, which has a composition shown in Table 3 below, was prepared.

TABLE 3

| Components | Contents (wt %) |
| --- | --- |
| 1. purified water | Balance |
| 2. glycerin | 8.0 |
| 3. butylene glycol | 4.0 |
| 4. hyaluronic acid extract | 5.0 |
| 5. beta-glucan | 7.0 |
| 6. carbomer | 0.1 |
| 7. sesamol derivatives | q.s. |
| 8. caprylic/capric triglyceride | 8.0 |
| 9. squalene | 5.0 |
| 10. stearyl glucoside | 1.5 |
| 11. sorbitan stearate | 0.4 |
| 12. cetearyl alcohol | 1.0 |
| 13. preservative | q.s. |
| 14. fragrance | q.s. |
| 15. pigment | q.s. |
| 16. triethanolamine | 0.1 |

FORMULATION EXAMPLE 2

Preparation of Nourishing Cream

Nourishing cream containing the sesamol derivatives prepared in Examples 1-3, which has a composition shown in Table 4 below, was prepared.

TABLE 4

| Components | Contents (wt %) |
| --- | --- |
| 1. Purified water | Balance |
| 2. glycerin | 3.0 |
| 3. butylene glycol | 3.0 |
| 4. liquid paraffin | 7.0 |
| 5. beta glucan | 7.0 |
| 6. carbomer | 0.1 |
| 7. sesamol derivatives | q.s. |
| 8. caprylic/capric triglyceride | 3.0 |
| 9. squalane | 5.0 |
| 10. cetearyl glucoside | 1.5 |
| 11. sorbitan stearate | 0.4 |
| 12. polysorbate | 1.2 |
| 13. preservative | q.s. |
| 14. fragrance | q.s. |
| 15. pigment | q.s. |
| 16. triethanolamine | 0.1 |

FORMULATION EXAMPLE 3

Preparation of Massage Cream

Massage cream containing the sesamol derivatives prepared in Examples 1-3, which has a composition shown in Table 5 below, was prepared.

TABLE 5

| Components | Content (wt %) |
| --- | --- |
| 1. purified water | balance |
| 2. glycerin | 8.0 |
| 3. butylene glycol | 4.0 |
| 4. liquid paraffin | 45.0 |
| 5. beta glucan | 7.0 |
| 6. carbomer | 0.1 |
| 7. sesamol derivatives | q.s. |
| 8. caprylic/capric triglyceride | 3.0 |
| 9. wax | 4.0 |
| 10. cetearyl glucoside | 1.5 |
| 11. sorbitan sesquioleate | 0.9 |
| 12. Vaseline | 3.0 |
| 13. preservative | q.s. |
| 14. fragrance | q.s. |
| 15. pigment | q.s. |
| 16. paraffin | 1.5 |

FORMULATION EXAMPLE 4

Preparation of Ointment

Ointment containing the sesamol derivatives prepared in Examples 1-3, which has a composition shown in Table 6 below, was prepared.

TABLE 6

| Components | Contents (wt %) |
| --- | --- |
| 1. purified water | Balance |
| 2. glycerin | 8.0 |

TABLE 6-continued

| Components | Contents (wt %) |
|---|---|
| 3. butylene glycol | 4.0 |
| 4. liquid paraffin | 15.0 |
| 5. beta glucan | 7.0 |
| 6. carbomer | 0.1 |
| 7. sesamol derivatives | q.s. |
| 8. caprylic/capric triglyceride | 3.0 |
| 9. squalene | 1.0 |
| 10. cetearyl glucoside | 1.5 |
| 11. sorbitan stearate | 0.4 |
| 12. cetearyl alcohol | 1.0 |
| 13. preservative | q.s. |
| 14. fragrance | q.s. |
| 15. pigment | q.s. |
| 16. wax | 4.0 |

The invention claimed is:

1. A sesamol derivative represented by Formula I, or its salt:

[Formula I]

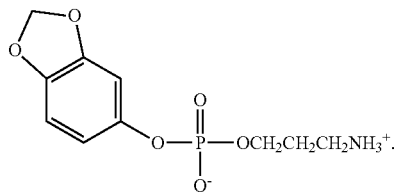

2. The sesamol derivative or its salt of claim 1, wherein said salt is an alkali metal salt or alkaline earth metal salt.

3. The sesamol derivative or its salt of claim 2, the alkali metal salt is a sodium salt or potassium salt, and the alkaline earth metal salt is a calcium salt.

4. A method for preparing a sesamol derivative or its salt according to claim 1, the method comprising the steps of:
(A) allowing sesamol and phosphorus oxychloride with react with each other at an equivalent ratio of 1:1-1.3 in an organic solvent in the presence of an organic base at a temperature of 12-18° C. for about 1-2 hours so as to prepare dichloro[3,4-methylene dioxyphenoxy]-phosphino-1-one;
(B) allowing the dichloro[3,4-methylene dioxyphenoxy]-phosphino-1-one produced in said step (A) to react with 3-aminopropanol in an organic solvent in the presence of a base so as to prepare [3,4-methylene dioxyphenoxy]-1,3,2-oxazaphosphorin P-oxide;
(C) filtering the reaction solution obtained in said step (B), concentrating the filtrate under reduced pressure, and then reacting the residue with an acid solution at a temperature of 5-100° C. for about 3-12 hours so as to hydrolyze the P—N bond of the residue, thus preparing sesamol, 3-aminopropane phosphoric acid diester; and
(D) crystallizing the sesamol, 3-aminopropane phosphoric by slowly adding a polar organic solvent dropwise thereto.

5. A skin external composition containing the sesamol derivative or its salt according to claim 1.

6. A skin external composition for antioxidant or anti-aging purposes, which contains the sesamol derivative or its salt according to claim 1.

* * * * *